United States Patent [19]

Manchand et al.

[11] Patent Number: 4,931,574

[45] Date of Patent: Jun. 5, 1990

[54] PROCESS FOR THE PREPARATION OF BENZOPYRANS

[75] Inventors: Percy S. Manchand, Montclair, N.J.; Robert A. Micheli, Kensington, Calif.

[73] Assignee: Hoffmann-La Roche Inc., Nutley, N.J.

[21] Appl. No.: 235,129

[22] Filed: Aug. 23, 1988

[51] Int. Cl.[5] .................. C07D 311/66; C07D 311/58
[52] U.S. Cl. ..................................... 549/405; 549/407
[58] Field of Search ................................ 549/407, 405

[56] References Cited

U.S. PATENT DOCUMENTS 4,728,650  3/1988  Eziri et al. ..................... 549/407
4,785,017  11/1988  Cohen et al. ................... 514/456

OTHER PUBLICATIONS

Roberts et al., "Basic Principles of Organic Chemistry", W. A. Benjamin, Inc., New York, NY, 1965, pp. 298–301.

Primary Examiner—Nicky Chan
Attorney, Agent, or Firm—George M. Gould; Bernard S. Leon; William G. Isgro

[57] ABSTRACT

The invention is directed to a process and intermediates for the preparation of benzopyrans such as racemic-6-acetyl-7-[5-(4-acetyl-3-hydroxy-2-propyl-phenoxy)pentyloxy]-3,4-dihydro-2H-1-benzopyran-2-carboxylic acid.

14 Claims, No Drawings

PROCESS FOR THE PREPARATION OF BENZOPYRANS

BRIEF SUMMARY OF THE INVENTION

The invention is directed to a process for the preparation of benzopyrans of the formula

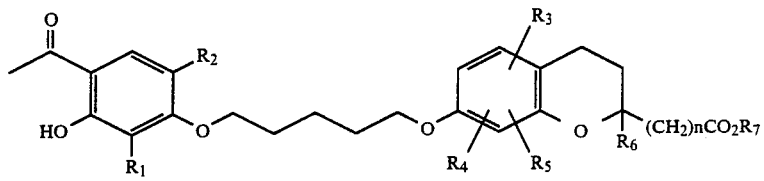

wherein $R_1$ is hydrogen or lower alkyl; $R_2$ is hydrogen or halogen; $R_3$, $R_4$ and $R_5$ are hydrogen, acyl or lower alkyl; $R_6$, $R_7$, independently, are hydrogen or lower alkyl; and n is an integer of 0-4, provided that only one of $R_3$, $R_4$ or $R_5$ can be acyl; enantiomers thereof, and, when $R_7$ is hydrogen, salts thereof with pharmaceutically acceptable bases.

The process comprises the steps of:

(a) reacting a compound of the formula

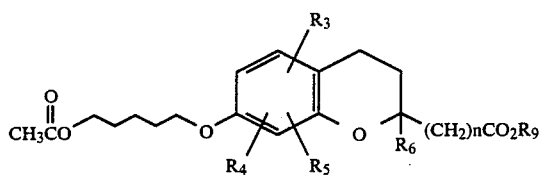

wherein $R_3$, $R_4$, $R_5$, $R_6$, and n are as described above, and $R_9$ is lower alkyl with a base to obtain a compound of the formula

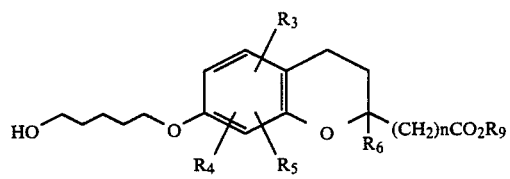

wherein $R_3$, $R_4$, $R_5$, $R_6$, $R_9$ and n are as described above;

(b) and reacting the product of step (a) with a sulfonating agent to obtain a compound of the formula

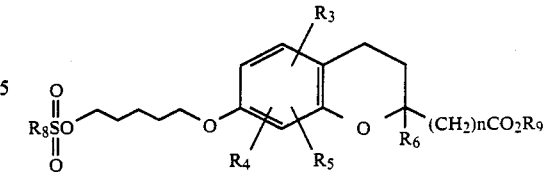

wherein $R_3$, $R_4$, $R_5$, $R_6$, $R_9$ and n are as described above and $R_8$ is methyl or p-methylphenyl;

(c) reacting the product of step (b) with a compound of the formula

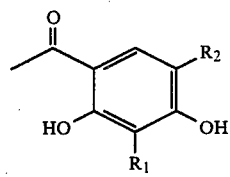

wherein $R_1$ is hydrogen or lower alkyl; and $R_2$ is hydrogen or halogen to yield a compound of the formula

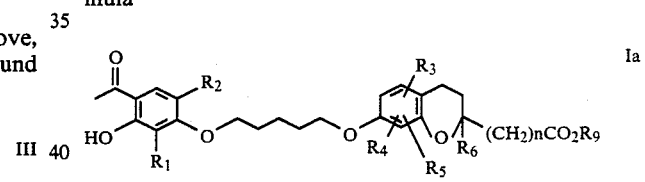

wherein $R_1$, $R_2$, $R_3$, $R_4$, $R_5$, $R_6$, $R_9$ and n are as described above, (d) optionally hydrolyzing the product of step (d) to obtain the corresponding carboxylic acid of formula

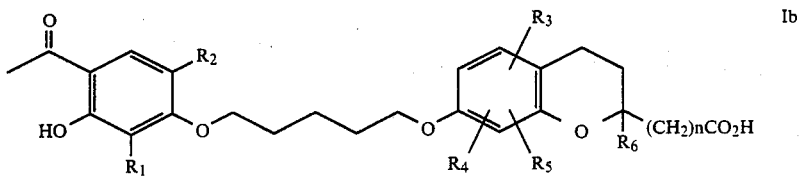

wherein $R_1$, $R_2$, $R_3$, $R_4$, $R_5$, $R_6$ and n are as described above.

In another aspect, the invention relates to intermediates of the formula

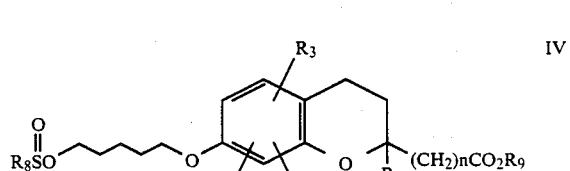

wherein $R_3$, $R_4$, $R_5$, $R_6$, $R_8$, $R_9$ and n are as described above.

DETAILED DESCRIPTION OF THE INVENTION

As used herein, the term "lower alkyl" denotes a straight or branched chain saturated hydrocarbon containing 1 to 7 carbon atoms, for example, methyl, ethyl, propyl, isopropyl, butyl, t-butyl, neopentyl, pentyl, heptyl and the like. The term "lower alkoxy" denotes a straight or branched chain lower alkoxy containing 1 to 7 carbon atoms, for example, methoxy, ethoxy, propoxy, t-butoxy and the like. The term "halogen" denotes all the halogens, that is, bromine, chlorine, fluorine and iodine. The term "acyl" denotes an "alkanoyl" group derived from an aliphatic carboxylic acid of 1 to 7 carbon atoms, for example, formyl, acetyl, propionyl and the like. The term "aryl" denotes phenyl or phenyl bearing 1 or more substituents, preferably up to 3 substituents, selected from the group consisting of halogen, trifluoromethyl, lower alkyl, lower alkoxy, nitro, amino, lower alkyl amino, and di-lower alkyl amino.

The invention comprises a process for the preparation of a compound of the formula

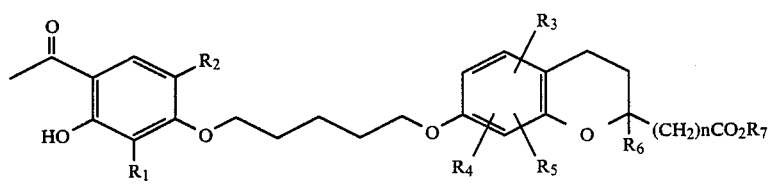

wherein $R_1$ is hydrogen or lower alkyl; $R_2$ is hydrogen or halogen; $R_3$, $R_4$, $R_5$ are hydrogen, acyl or lower alkyl; $R_6$ and $R_7$, independently are hydrogen or lower alkyl; and n is an integer of 0–4, provided that only one of $R_3$, $R_4$, $R_5$ can be acyl; enantiomers thereof, and, when $R_7$ is hydrogen, salts thereof with pharmaceutically acceptable basis.

Compounds of formula I are described in U.S. application Ser. No. 614,368, filed May 29, 1984. Ser. No. 614,368 is hereby incorporated by reference.

to prepare a compound of formula I by the process of the invention, tetrahydropyran is reacted with the acid halide acetyl bromide under an inert atmosphere such as nitrogen in the presence of a catalyst such as zinc bromide, to obtain 5-bromo-1-pentanyl acetate which in turn is reacted with a phenol of the formula

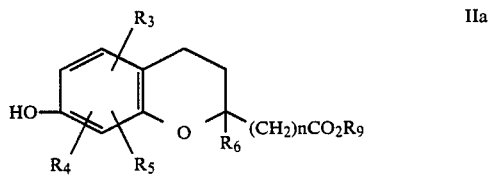

wherein $R_3$, $R_4$, and $R_5$ are hydrogen, acyl, or lower alkyl; $R_6$ is hydrogen or lower alkyl; $R_9$ is lower alkyl; and n is an integer of 0–4, which is known or can be prepared in accordance with known methods, to obtain a compound of formula

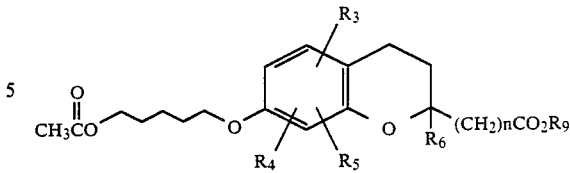

wherein $R_3$, $R_4$, $R_5$, $R_6$, and n are as described above, and $R_9$ is lower alkyl, A compound of formula II is in turn reacted with a base to obtain a compound of formula

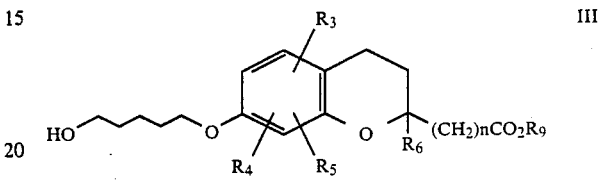

wherein $R_3$, $R_4$, $R_5$, $R_6$, $R_9$ and n are as described above;

(b) the product of step (a) is reacted with a sulfonating agent to obtain a compound of formula

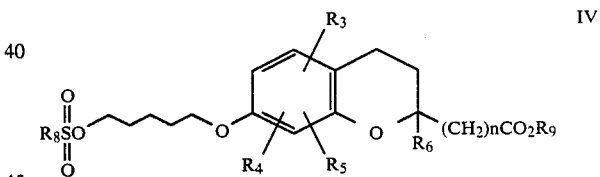

wherein $R_3$, $R_4$, $R_5$, $R_6$, $R_9$ and n are as described above and $R_8$ is lower alkyl or aryl;

(c) the product of step (b) is reacted with a compound of formula

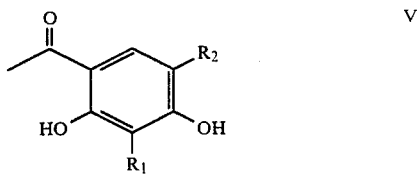

wherein $R_1$ and $R_2$ are as described above, to obtain a compound of the formula

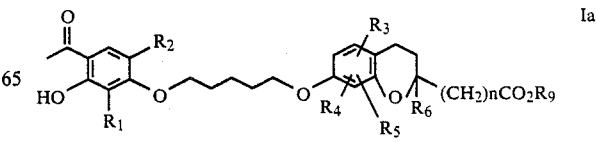

wherein $R_1$, $R_2$, $R_3$, $R_4$, $R_5$, $R_6$, $R_9$ and n are as described above (d) and optionally treating the product of step (c) with a base to obtain a compound of the formula

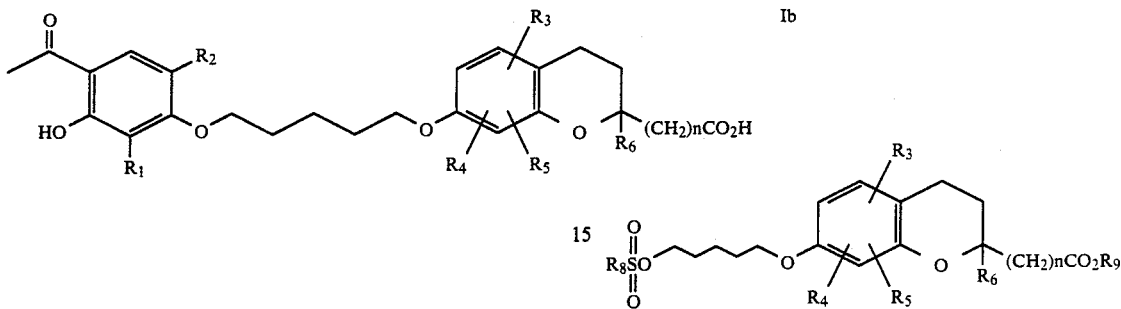

Ib wherein $R_1$, $R_2$, $R_3$, $R_4$, $R_5$, $R_6$ and n are as described above.

As can be seen, compounds of formula Ia and Ib are encompassed by formula I.

In accordance with the invention, a compound of formula

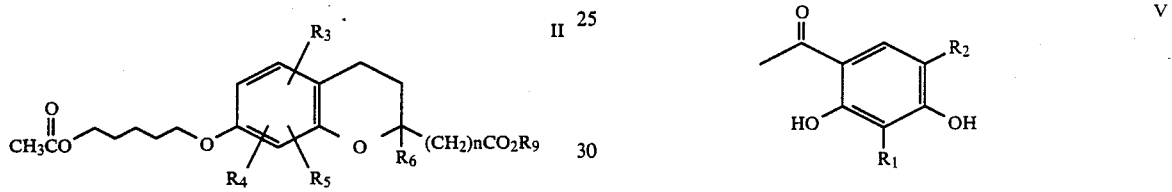

II wherein $R_3$, $R_4$, $R_5$, $R_6$, $R_9$ and n are as described above can be prepared in accordance with known methods, is reacted with a hydrolyzing agent such as an acid like borontrifluoride etherate, Dowex cation exchange resin, p-toluenesulfonic acid, or a base such as potassium hydroxide, potassium bicarbonate, sodium methoxide, potassium cyanide, benzyltrimethylammonium hydroxide, tetrabutylammonium methoxide, or more preferably, tetrabutylammonium hydroxide in a polar, protic organic solvent such as ethanol, or more preferably, methanol at 10° to about 50° under an inert atmosphere such as argon or more preferably nitrogen, at about 2 minutes to about 2 hours to obtain a compound of the formula

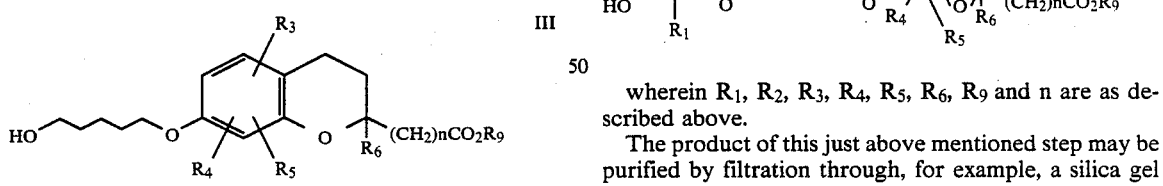

III wherein $R_3$, $R_4$, $R_5$, $R_6$, $R_9$ and n are as described above.

The compound of formula III may be isolated, or alternatively may be converted without isolation into the next compound in the synthetic scheme.

A compound of formula III is sulfonated with a sulfonating agent such as an arylsulfonyl chloride like p-toluenesulfonyl chloride, or more preferably an alkyl sulfonyl chloride like methane sulfonyl chloride in the presence of an organic base such as pyridine, or more preferably triethylamine, under an inert atmosphere such as argon or nitrogen, at −10° to 10° C., for about 5 minutes to 2 hours to obtain a compound of formula

IV wherein $R_3$, $R_4$, $R_5$, $R_6$, $R_9$, n, and $R_8$ are as described above.

The compound of formula IV may be reacted with a compound of formula

V wherein $R_1$ and $R_2$ are as described above in a polar, aprotic organic solvent such as dimethyl sulfoxide, or dimethyl formamide. Alternatively, the reaction may be carried out in an aprotic, nonpolar organic solvent such as xylene or more preferably toluene in the presence of potassium carbonate and a phase transfer catalyst such as tetrabutylammonium chloride, or more preferably, tris(3,6-dioxaheptyl)amine under an inert atmosphere such as argon or nitrogen, at about 30° to about reflux temperature of the solvent, for about 1 to about 30 hours to obtain a compound of the formula Ia wherein $R_1$, $R_2$, $R_3$, $R_4$, $R_5$, $R_6$, $R_9$ and n are as described above.

The product of this just above mentioned step may be purified by filtration through, for example, a silica gel filter.

A compound of formula Ia is converted to a compound of formula Ib by conventional hydrolysis agents such as p-toluenesulfonic acid, or more preferably a base like aqueous sodium hydroxide in a polar, protic organic solvent such as ethanol, or more preferably methanol under an inert atmosphere at about 30° to about reflux temperature of the solvent system. The invention more preferably relates to the above-described process for preparing compounds of formula I wherein $R_1$ is lower alkyl, $R_2$ is hydrogen, $R_3$ is acyl; $R_4$, $R_5$, $R_6$ and $R_7$ are hydrogen.

The invention still more preferably relates to the above-described process for preparing compounds of formula I wherein $R_1$ is propyl, $R_2$ is hydrogen, $R_3$ is acetyl, $R_4$, $R_5$, $R_6$ and $R_7$ are hydrogen.

A most preferred compound prepared by the above-described process is rac-6-acetyl-7-[5-(4-acetyl-3-hydroxy-2-propylphenoxy)pentyloxy]-3,4-dihydro-2H-1-benzopyran-2-carboxylic acid.

As can be seen, formula I encompasses compounds of formula Ia and Ib.

Compounds of formula I are useful as antiallergic agents.

A compound of formula I, an enantiomer thereof or a salt thereof when $R_7$ is hydrogen, or a composition containing a therapeutically effective amount of a compound of formula I, an enantiomer thereof or a salt thereof when $R_7$ is hydrogen, can be administered by methods well known in the art. Thus, a compound of formula I, an enantiomer thereof or a salt thereof, when $R_7$ is hydrogen, can be administered either singly or with other pharmaceutical agents, for example, antihistamines, mediator release inhibitors, methyl xanthines, $\beta$-agonists or anti asthmatic steroids such as prednisone and prednisolone orally, parenterally, rectally, or by inhalation, for example, in the form of an aerosol, micropulverized powder or nebulized solution.

Presently, the most preferred route of administration for the compounds of formula I is by inhalation, for example, as an aerosol, and particularly for use as an anti asthmatic agent.

For oral administration they can be administered in the form of tablets, capsules, for example, in admixture with talc, starch, milk sugar or other inert ingredients, that is, pharmaceutically acceptable carriers, or in the form of aqueous solutions, suspensions, elixirs or aqueous alcoholic solutions, for example, in admixture with sugar or other sweetening agents, flavoring agents, colorants, thickeners and other conventional pharmaceutical excipients.

For parenteral administration, they can be administered in solutions or suspension, for example, as an aqueous or peanut oil solution or suspension using excipients and carriers conventional for this mode of administration.

For administration as aerosols, they can be dissolved in a suitable pharmaceutically acceptable solvent, for example, ethyl alcohol or combinations of miscible solvents, and mixed with a pharmaceutically acceptable propellant. Such aerosol compositions are packaged for use in a pressurized container fitted with an aerosol valve suitable for release of the pressurized composition. Preferably, the aerosol valve is a metered valve, that is one which on activation releases a predetermined effective dose of the aerosol composition.

The final products of the invention can also be pharmaceutically acceptable salts of formulas I and their enantiomers, when $R_7$ is hydrogen. Said salts can be prepared by reacting an acid of formula I or an enantiomer thereof with a base having a non-toxic, pharmacologically and pharmaceutically acceptable cation. In general, any base which will form a salt with a carboxylic acid and whose pharmacological properties will not cause an adverse physiological effect when ingested by a warm-blooded animal is considered as being within the scope of the final products produced by the process of the invention.

Suitable bases thus include, for example, alkali metal and alkaline earth metal hydroxides or carbonates, such as, sodium hydroxide, potassium hydroxide, calcium hydroxide, potassium carbonate and the like, ammonia, primary, secondary and tertiary amines such as monoalkylamines, dialkylamines, trialkylamines, nitrogen containing heterocyclic amines, for example, piperidine, basic amino acids such as lysine and the like.

The pharmaceutically acceptable salts thus produced are the functional equivalent of the corresponding benzopyrans of formula I and their enantiomers and one skilled in the art will appreciate that, to the extent that the salts produced by the process of the invention are useful in therapy, the variety of salts is only limited by the criterion that the bases employed in forming the salts be both non-toxic and physiologically acceptable.

The dose of a compound of formula I, an enantiomer thereof, or a salt thereof, when $R_7$ is hydrogen, to be administered and the frequency of administration will be dependant on the potency and duration of activity of the particular compound of formula I, an enantiomer or salt thereof to be administered and on the route of administration, as well as the severity of the condition, age of the warm-blooded animal to be treated and the like. Doses of a compound of formula I, an enantiomer thereof or a salt thereof, when $R_7$ is hydrogen, contemplated for use in the practice of the invention are in the range from about 25 to about 1,000 mg per day, preferably about 25 to about 250 mg either as a single dose or in divided doses per day.

The resolution of compounds of formula I are disclosed in U.S. Ser. No. 614,368.

The examples which follow further illustrate the disclosure. All temperatures are in °C. unless otherwise stated.

EXAMPLE 1

Preparation of 5-bromo-1-pentanyl acetate

A 2 L three-neck, round-bottom flask equipped with a mechanical stirrer, a condenser and a nitrogen bubbler, was charged with 430.7 g (5.00 moles) of tetrahydropyran, 399.6 g (3.25 moles) of acetyl bromide, and 1.13 g of zinc bromide. The mixture was stirred under nitrogen at reflux for 2.5 hours, cooled to room temperature (ice bath), and transferred to a separatory funnel with 1 L of hexanes. The solution was washed with 250 mL of saturated aqueous sodium bicarbonate, 2×500 mL=1 L of deionized water, 500 mL of saturated brine, dried (anhydrous sodium sulfate) and filtered. The solvent was removed at 40°/70 mm to give 692 g of crude 5-bromo-1-pentanyl acetate as a dark liquid. Distillation using a 32 cm Goodloe column gave 625.6 g (92% yield) of 5-bromo-1-pentanyl acetate as a colorless liquid, bp 60°–67°/0.08 mm.

Calcd for $C_7H_{13}BrO_2$: C 40.21; H, 6.27; Br, 38.22. Found: C, 39.72; H, 6.35; Br, 38.45.

EXAMPLE 2

Preparation of rac-6-Acetyl-3,4-dihydro-7-[(5-acetoxypentyl)oxy]-2H-1-benzopyran-2-carboxylic Acid Methyl Ester A 12-L three-neck, round-bottom flask equipped with a mechanical stirrer and a nitrogen bubbler, was charged with 375.0 g (1.79 moles) of 5-bromo-1-pentanyl acetate, 3.5 L of dimethyl sulfoxide, 407.0 g (1.63 moles) of rac-6-acetyl-3,4-dihydro-7-hydroxy-2H-1-benzopyran-2-carboxylic acid methyl ester and 510.0 g of anhydrous granular potassium carbonate in finely powdered form. The mixture was stirred at room temperature under nitrogen for 19 hours, poured into an extractor containing 10 L of deionized water, and extracted with 2×4 L and 1×2 L=10 L of ethyl acetate. The organic layer was washed with 2×4 L=8 L of 1:1 deionized water-saturated brine, followed by 2 L of saturated brine, dried (anhydrous sodium sulfate), and filtered. The solvent was removed at 45°/70 mm and then under high vacuum to give 648.3 g of crude rac-6-acetyl-3,4-dihydro-7-[(5-acetoxypentyl)oxy]-2H-1-benzopyran-2-carboxylic acid methyl ester. The crude product was dissolved in 2 L of anhydrous ether and the solution was poured into a 12 L three-neck flask equipped with a mechanical stirrer. The stirred solution was cooled in an ice-bath and 2 L of petroleum ether (35°–60°) was slowly added, which resulted in the formation of a precipitate heavy enough to stop the stirrer. The solid was broken with a spatula and stirring was continued in the ice-bath for 1 hour. The product was collected by filtration, washed with cold (3°) 1:1 ether-petroleum ether, and dried at room temperature under high vacuum to give 601.5 g (97.7% yield) of rac-6-acetyl-3,4-dihydro-7-[(5-acetoxypentyl)oxy]-2H-1-benzopyran-2-carboxylic acid methyl ester as a white powder, mp 37°–49° C. UV (EtOH): λ max, 312 ($\epsilon$=7,200), 268 ($\epsilon$=11,200), 230 ($\epsilon$=16,900), and 216 ($\epsilon$=19,000) nm; MS: m/z 378 (M+, 40).

Calcd for $C_{20}H_{26}O_7$: C, 63.48; H, 6.93; Found: C, 63.12 H, 7.19

EXAMPLE 3

Preparation of rac-6-Acetyl-3,4-dihydro-7[5-[(methylsulfonyl)-oxy]-pentyloxy]-2H-1-benzopyran-2-carboxylic Acid Methyl Ester A 12 L three-neck, round-bottom flask equipped with a mechanical stirrer, a dropping funnel and a nitrogen bubbler was charged with 340.0 g (0.90 mole) of rac-6-acetyl-3,4-dihydro-7-[(5-acetoxypentyl)]oxy]-2H-1-benzopyran-2-carboxylic acid methyl ester. A total of 6.8 L of methanol was added and the mixture was stirred at room temperature under a nitrogen atmosphere for 10 minutes until a complete solution was obtained. A total of 180 mL of 1M tetrabutylammonium hydroxide in methanol was added over 15 minutes from the dropping funnel and the reaction mixture was stirred at room temperature for 4.5 hours at which time thin layer chromatography (60% ethyl acetate in hexanes) indicated that the reaction was complete. The pH of the reaction mixture was then adjusted to pH=6 by the addition of 8 mL of glacial acetic acid. The methanol was removed at 40°/70 mm and the residue was transferred to a separatory funnel using 3 L of ethyl acetate. The solution was washed with 600 mL of 0.5N hydrochloric acid solution, 2×600 mL=1.2 L of 1:1 deionized water-saturated brine, 600 mL of saturated aqueous sodium bicarbonate, 2×600 mL=1.2 L of 1:1 deionized water-saturated brine, and 600 mL of saturated brine. The organic layer was dried (anhydrous sodium sulfate), and filtered into a 12 L three-neck flask equipped with a mechanical stirrer, a dropping funnel and a nitrogen bubbler, and evaporated to give a gum, which solidified on refrigeration for two days. Crystallization was induced by the careful addition of hexanes to a cold solution of the gum in ethyl acetate, to give rac-6-acetyl-3,4-dihydro-7-[(5-hydroxypentyl)oxy]-2H-1-benzopyran-2-carboxylic acid methyl ester, mp 58°–62° C. The amounts of the solvents used were such that there was about 70% ethyl acetate in hexanes. Returning to the original reaction being described in Example 3, about 4 L of solution of this alcohol in ethyl acetate was cooled in an ice bath and stirred under a nitrogen atmosphere. A total of 750 mL of triethylamine was added in one portion followed by the addition of 160 mL of methanesulfonyl chloride over a 20 minute period. After stirring for 30 minutes in the ice bath, thin layer chromatography showed the reaction to be incomplete. A total of 40 mL of methanesulfonyl chloride was added over 5 minutes and after stirring in the ice-bath for an additional 90 minutes, the reaction was still incomplete. Then 100 mL of triethylamine was added in one portion and 80 mL of methanesulfonyl chloride was added over 10 minutes and stirring was continued in the ice-bath for an additional 40 minutes, at which time the reaction was complete as indicated by thin layer chromatography (60% ethyl acetate in hexane). During this reaction, additional triethylamine was needed to keep a basic reaction medium. The reaction mixture was transferred to a separatory funnel, and was washed with 1 L of 2N hydrochloric acid solution, 2×1 L=2 of 1:1 deionized water-saturated brine, 1 L of saturated brine and dried over anhydrous sodium sulfate. The solution was filtered, concentrated at 40° C/70 mm to about 1530 mL, and then heated to boiling on a steam bath. A total of 1020 mL of hexanes was added and the solution was allowed to cool to room temperature. Crystallization was induced by scratching with a glass rod while cooling. After standing at room temperature for 4 hours, the mixture was refrigerated overnight to complete the crystallization process. The crystals were collected by filtration, washed with 200 mL of cold 4:3 ethyl acetate-hexanes, and dried in vacuo at room temperature under 0.5 mm high vacuum to give 317.1 g (85.2% yield) of rac-6-acetyl-3,4-dihydro-7-[5-[(methylsulfonyl)-oxy]-pentyloxy]-2H-1-benzopyran-2-carboxylic acid methyl ester, mp 73°–76° C., as a white powder, homogeneous by thin layer chromatography (60% ethyl acetate in hexanes).

UV (EtOH)λ max 313 ($\epsilon$=6,980), 268 ($\epsilon$=16,020) nm; MS: m/z 414 (M+, 20).

Calcd for $C_{19}H_{26}O_8S$: C, 55.06; H, 6.32; Found: C, 55.24; H, 6.44.

EXAMPLE 4

Preparation of rac-6-acetyl-7-[5-(4-acetyl-3-hydroxy-2-propylphenoxy)pentyloxy]-3,4-dihydro-2H-1-benzopyran-2-carboxylic acid methyl ester A 12-L three-neck flask equipped with a mechanical stirrer, a reflux condenser and a nitrogen bubbler, was charged with 317.1 g (0.76 mole) of rac-6-acetyl-3,4-dihydro-7-[5-[(methylsulfonyl)oxy]pentyloxy]-2H-1-benzopyran-2-carboxylic acid methyl ester, 3.4 L of toluene, 146.5 g (0.76 mole) of 2',4'-dihydroxy-3'-propylacetophenone, 154.2 g of anhydrous granular potassium carbonate in finely powdered form, and 16.1 g of tris (3,6-dioxaheptyl)amine which will be referred to as TDA-1. The mixture was stirred under nitrogen at reflux for 6.5 hours. After cooling to room temperature, the mixture was poured into an extractor containing 2 L of 1:1 deionized water-saturated brine, and the organic phase was collected. The aqueous layer was then re-extracted with 1 L of toluene. The combined organic extracts were washed with 3×2 L=6 L of 1:1 deionized water-saturated brine, and 2 L of saturated brine. The organic phase was dried (anhydrous sodium sulfate), filtered, and concentrated at 55°/70 mm to a volume of about 1.5 L. The yellow solution was slurried with 392 g of 70-230 mesh silica gel 60 and poured into a scintered glass funnel containing 784 g of silica gel 60. The product was eluted using a slight vacuum as follows:

| Fraction | Volume | Solvent Mixture |
|---|---|---|
| 1 | 8 L | 4 L toluene, followed by 4 L of 2.5% acetate in toluene |
| 2 | 8 L | 5% ethyl acetate in toluene |
| 3 | 8 L | 7.5% ethyl acetate in toluene |

After analysis by thin layer chromatography (40% ethyl acetate in hexanes) and high pressure liquid chromatography of an aliquot from each fraction and of the crude reaction mixture, fractions 1, 2, and 3 were combined. Evaporation at 55°/70 mm and then at 55°/0.5 mm gave 323.0 g of racemic-6-acetyl-7-[5-(4-acetyl-3-hydroxy-2-propylphenoxy)pentyloxy]-3,4-dihydro-2H-1-benzopyran-2-carboxylic acid methyl ester as a pale yellow oil. This solid was dissolved in 1750 mL of boiling methanol on a steam bath. The solution was transferred to a 12 L battery jar, cooled to room temperature over 5 hours and stored at 3° overnight to effect crystallization. A battery jar was used to facilitate the transfer of the solid to the funnel for filtration. The colorless solid was collected by filtration, washed with 200 mL of cold (−20°) methanol, and dried in vacuo at room temperature under high vacuum to give 314.0 g (80% yield) of rac-6-acetyl-7-[5-(4-acetyl-3-hydroxy-2-propylphenoxy)pentyloxy]-3,4-dihydro-2H-1-benzopyran-2-carboxylic acid methyl ester which was 99.4% pure by high pressure liquid chromatography. (In a separate example, 61.07 g of rac-6-acetyl-7-[5-(4-acetyl-3-hydroxy-2-propylphenoxy)pentyloxy]-3,4-dihydro-2H-1-benzopyran-2-carboxylic acid methyl ester obtained after crystallization from methanol was dissolved in 600 mL of warm ether, diluted with 100 mL of hexanes, cooled to 0° C. and seeded. The mixture was refrigerated overnight, the product was collected by filtration, and washed with cold, 0° C., 5.2 ether: hexanes. After drying in vacuo at room temperature overnight, 56.12 g of rac-6-acetyl-7-[5-(4-acetyl-3-hydroxy-2-propylphenoxy)pentyloxy]-3,4-dihydro-2H-1-benzopyran-2-carboxylic acid methyl ester of mp 77°–80° C. was obtained.)

EXAMPLE 5

Preparation of rac-sodium-6-acetyl-7-[5-(4-acetyl-3-hydroxy-2-propylphenoxy)pentyloxy]-3,4-dihydro-2H-1-benzopyran-2-carboxylate monohydrate A 12 L three-neck flask equipped with a mechanical stirrer, a reflux condenser and a nitrogen bubbler, was charged with 314.0 g (0.61 mole) of rac-6-acetyl-7-[5-(4-acetyl-3-hydroxy-2-propylphenoxy)pentyloxy]-3,4-dihydro-2H-1-benzopyran-2-carboxylic acid methyl ester and 4.8 L of methanol. The mixture was heated to reflux to give a yellow solution. A solution of 25.3 g (0.63 mole) of sodium hydroxide pellets in 105 mL of deionized water was added in one portion and the reaction mixture was boiled at reflux under nitrogen for 1 hour. The solution was concentrated at 50°/70 mm on a rotary evaporator to a volume of 2.4 L and was then transferred to a battery jar. A total of 2.4 L of anhydrous ether was cautiously added, and the mixture was stirred for 15 minutes while cooling to room temperature. The solution was then stored at 3° overnight to effect crystallization. The solid was collected by filtration, washed with 2 L of cold (3°) 3:1 ether-methanol, and dried at room temperature in a vacuum oven under high vacuum to give (62% yield) of rac-sodium-6-acetyl-7-[5-(4-acetyl-3-hydroxy-2-propylphenoxy)pentyloxy]-3,4-dihydro-2H-1-benzopyran-2-carboxylate monohydrate as a white solid, homogeneous by thin layer chromatography and with an Rf 0.52. Rac-6-acetyl-7-[5-(4-acetyl-3-hydroxy-2-propylphenoxy)pentyloxy]-3,4-dihydro-2H-1-benzopyran-2-carboxylic acid methyl ester had Rf 0.64. The solvent system used in the thin layer chromatography was toluene-ethyl acetate-acetic acid (65:25:10).

We claim:

1. A process for preparing a compound of the formula

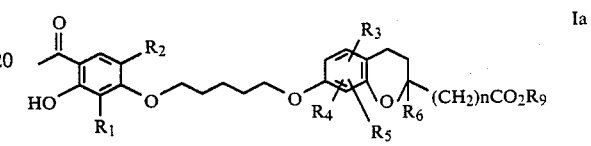

wherein $R_1$ is hydrogen or lower alkyl; $R_2$ is hydrogen or halogen; $R_3$, $R_4$ and $R_5$ are hydrogen, acyl or lower alkyl; $R_6$ is hydrogen or lower alkyl; $R_9$ is lower alkyl and n is an integer of 0-4; provided that only one of $R_3$, $R_4$ or $R_5$ can be acyl; enantiomers thereof, or a salt thereof, which comprises (a) reacting a compound of the formula

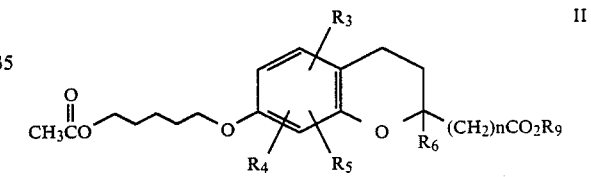

wherein $R_3$, $R_4$, $R_5$, $R_6$, $R_9$, and n are as described above with a base in a polar, protic organic solvent to obtain a compound of the formula

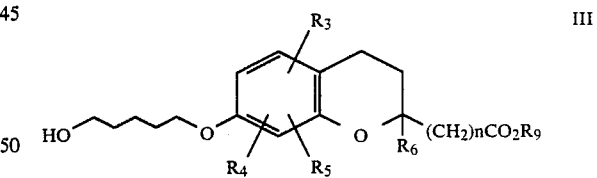

wherein $R_3$, $R_4$, $R_6$, $R_6$, $R_9$ and n are as described above;

(b) reacting the product of step (a) with a sulfonating agent in a polar organic solvent to obtain a compound of the formula

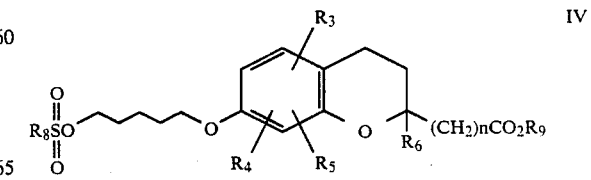

wherein $R_3$, $R_4$, $R_5$, $R_6$, $R_9$ and n are as described above, and $R_8$ is lower alkyl or aryl;

(c) reacting the product of step (b) with a compound of the formula

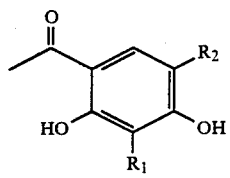

wherein $R_1$ and $R_2$ are as described above in a polar, aprotic organic solvent or in a nonpolar aprotic organic solvent in the presence of a base to obtain a compound of the formula

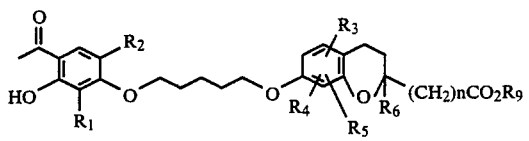

wherein $R_1$, $R_2$, $R_3$, $R_4$, $R_5$, $R_6$, $R_9$ and n are as described above.

2. A process according to claim 1, for preparing a compound of formula I wherein $R_1$ is lower alkyl, $R_2$ is hydrogen, $R_3$ is acyl; $R_4$, $R_5$ and $R_6$ are hydrogen, and $R_9$ is lower alkyl.

3. A process according to claim 2, for preparing a compound of formula I wherein $R_1$ is propyl, $R_2$ is hydrogen, $R_3$ is acetyl; $R_4$, $R_5$, and $R_6$ are hydrogen, and $R_9$ is lower alkyl.

4. A process according to claim 3, for preparing the compound of formula I, rac-6-acetyl-7-[5-(4-acetyl-3-hydroxy-2-propylphenoxy)pentyloxy]-3,4-dihydro-2H-1-benzopyran-2-carboxylic acid methyl ester.

5. A process according to claim 1, wherein the base is tetrabutyl ammonium hydroxide.

6. A process according to claim 1, wherein the polar protic organic solvent of step (a) is methanol.

7. A process according to claim 1, wherein the sulfonating agent of step (b) is methane sulfonyl chloride.

8. A process according to claim 1, wherein the polar organic solvent of step (b) is pyridine.

9. A process according to claim 1, wherein step (c) is carried out in the presence of the phase transfer catalyst tris(3,6-dioxaheptyl)amine.

10. A process according to claim 1, wherein the solvent of step (c) is toluene.

11. A process according to claim 1, which further comprises hydrolyzing the product of step (c) to obtain a compound of formula

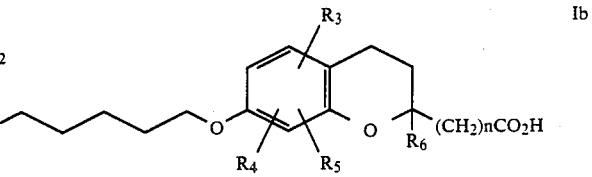

wherein $R_1$, $R_2$, $R_3$, $R_4$, $R_5$, $R_6$ and n are as described above.

12. A process according to claim 11, wherein the hydrolyzing agent is aqueous sodium hydroxide.

13. A process for preparing a compound of the formula

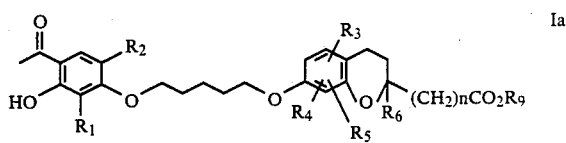

wherein $R_1$ is hydrogen or lower alkyl; $R_2$ is hydrogen or halogen, $R_3$, $R_4$ and $R_5$ are hydrogen, acyl, or lower alkyl; $R_6$ is hydrogen or lower alkyl; $R_9$ is lower alkyl, and n is an integer of 0–4; provided that only one of $R_3$, $R_4$ or $R_5$ can be acyl which comprises reacting a compound of the formula

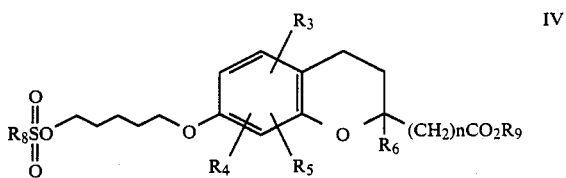

wherein $R_3$, $R_4$, $R_5$, $R_6$, $R_9$ and n are as described above and $R_8$ is lower alkyl or aryl with a compound of the formula

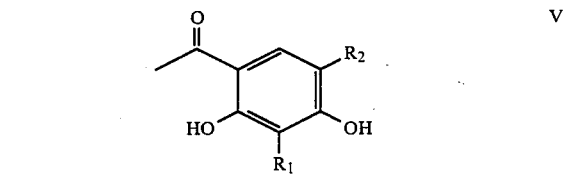

wherein $R_1$ and $R_2$ are as described above, in a polar, aprotic organic solvent or in a nonpolar aprotic organic solvent in the presence of a base and the phase transfer catalyst tris(3,6-dioxaheptyl)amine.

14. A process according to claim 13, wherein the organic solvent is toluene.

* * * * *

UNITED STATES PATENT AND TRADEMARK OFFICE
CERTIFICATE OF CORRECTION

PATENT NO. : 4,931,574
DATED : June 5, 1990
INVENTOR(S) : Percy S. Manchand and Robert A. Micheli It is certified that error appears in the above-identified patent and that said Letters Patent is hereby corrected as shown below:

In claim 1, column 12, line 53, first occurrence, please change "$R_6$" to -- $R_5$ --.

Signed and Sealed this

Fifth Day of November, 1991

Attest:

HARRY F. MANBECK, JR.

Attesting Officer

Commissioner of Patents and Trademarks